United States Patent [19]
Carl

[11] Patent Number: 5,497,670
[45] Date of Patent: Mar. 12, 1996

[54] LIQUID DISPENSING APPARATUS INCLUDING MEANS FOR LOADING PIPETTE TIPS ONTO LIQUID DISPENSING CYLINDERS AND MAINTAINING THE LOADING FORCE DURING THE APPARATUS OPERATION CYCLE

[76] Inventor: Richard A. Carl, 30833 Rue Valois, Rancho Palos Verdes, Calif. 90274

[21] Appl. No.: 414,225

[22] Filed: Mar. 31, 1995

[51] Int. Cl.⁶ .................. G01N 1/14; B01L 3/02
[52] U.S. Cl. .................... 73/863.32; 73/864.14; 73/864.17
[58] Field of Search ............ 73/863.32, 864.14, 73/864.17, 864.23

[56] References Cited

U.S. PATENT DOCUMENTS

| | | | |
|---|---|---|---|
| 3,776,700 | 12/1973 | Gallant | 73/863.32 X |
| 4,478,094 | 10/1984 | Salomaa et al. | 73/863.32 |
| 4,555,957 | 12/1985 | Frankel et al. | 73/864.14 |
| 4,936,152 | 6/1990 | Aldred | 73/863.32 |
| 5,021,217 | 6/1991 | Oshikubo | 73/863.32 X |
| 5,190,727 | 3/1993 | Hirsch | 73/864.14 X |
| 5,226,426 | 7/1993 | Yoon | 128/753 |

Primary Examiner—Thomas P. Noland

[57] ABSTRACT

A compact, lightweight apparatus for introducing a measured amount of liquid into receptacles positioned in a microtiter plate through disposable pipettes loaded in a sealed manner on the front end of dispensing air cylinders positioned in the apparatus. The pipettes, corresponding in number to the number of cylinders, are positioned in a carrier tray below the cylinders. The carrier tray is moved in an upward direction by another air cylinder with a sufficient loading force such that the pipettes are sealed to the front end of the adjacent cylinder. The loading force is maintained during the entire operating sequence of the apparatus ensuring that the pipette tips always have an effective seal with its cylinder. O-rings positioned in the carrier tray act as individual springs for each of the individual pipette tips to provide a cushioning effect between the pipette and the adjacent cylinder to compensate for molding variations and other dimensional variations in the pipette tips. The pipette tips are removed from the cylinders, when required by the user, by the same assembly that loaded the pipette tips. The pipette loading sequence then can be repeated.

7 Claims, 3 Drawing Sheets

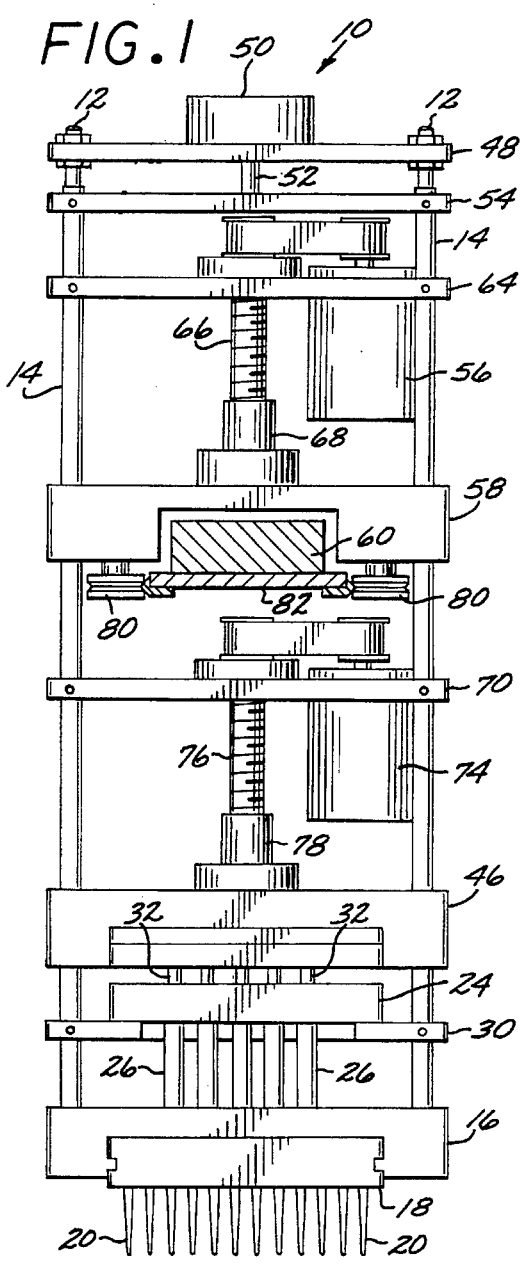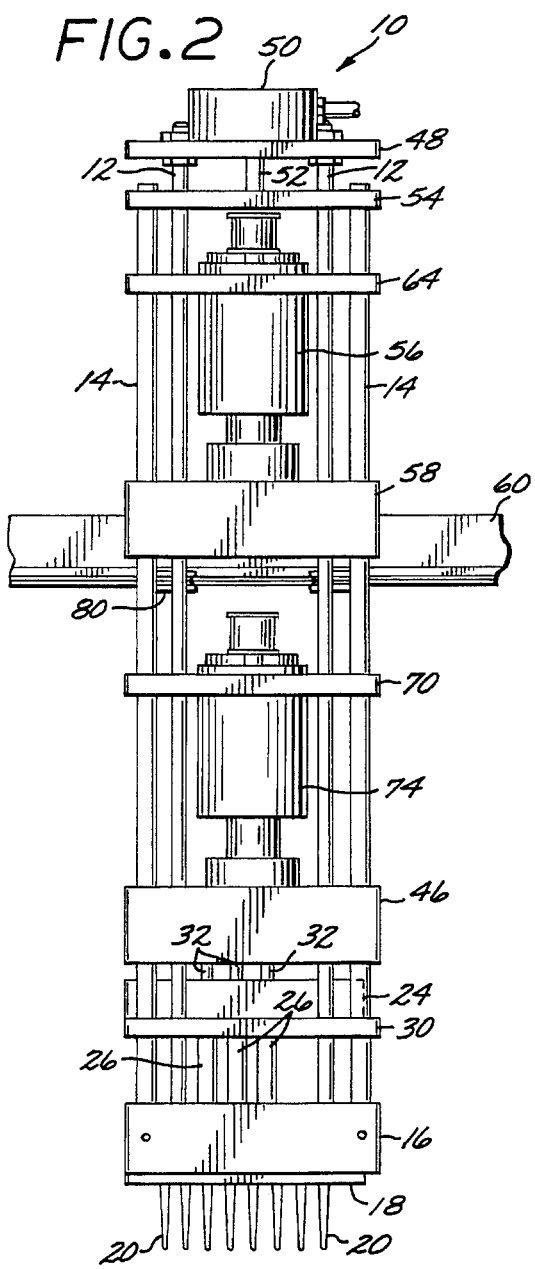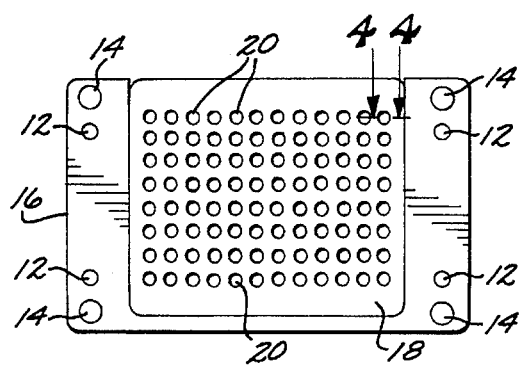

LIQUID DISPENSING APPARATUS INCLUDING MEANS FOR LOADING PIPETTE TIPS ONTO LIQUID DISPENSING CYLINDERS AND MAINTAINING THE LOADING FORCE DURING THE APPARATUS OPERATION CYCLE

BACKGROUND OF THE INVENTION

1. Field of the Invention

The present invention provides improved apparatus for dispensing controlled amounts of liquid into receptacles, the apparatus including means for loading disposable pipette tips onto fluid loading/dispensing cylinders and maintaining a positive pressure load on the tips during introduction of the liquid into the pipette tips and dispensing of the liquid thereafter into the receptacles, thereby providing an effective liquid seal between the pipette tips and cylinders during the operation cycle of the apparatus.

2. Description of the Prior Art

U.S. Pat. No. 5,226,426, assigned to the assignee of the present invention, describes a positive displacement apparatus for introducing measured amounts of liquid into receptacles. A liquid supply comprises pistons and cylinders and means are provided to move the cylinders upwardly and downwardly with respect to the receptacles, the former movement drawing liquid into the cylinders, the latter movement expelling liquid from the cylinders. Permanently attached needles are provided to expel air trapped in the cylinders and project into the base of cylinders and project into either the liquid supply or the receptacles, depending upon which part of cycle the machine is operating on.

Although the '462 patent utilizes a fixed needle arrangement, other fluid dispensing system use fluid containing plastic pipette tips, the tips being joined to a metal dispensing cylinder by positioning a tray of pipette tips below the cylinders and then moving the tray upwards towards the coaligned cylinders by an actuator located on or beneath the tray supporting table until the tips are secured to the adjacent cylinder. This design causes a significant amount of force to be exerted up into the associated dispensing heads and into the supporting structure. This in turn necessitates that the structure be large to support the force, a typical structure being in the form of a large "C", the force being applied to the open part of the "C" causing the remaining closed part to be very large. In addition, to the inherent disadvantages of utilizing large structures, the fact that the initially loading force is eventually removed increasing, the likelihood that the original seal formed between the plastic pipette tip and the metal cylinder will be broken during the loading and dispensing operation being limits the usefulness of the prior art devices.

What is desired therefore is to provide a compact, relatively lightweight apparatus for securing pipette tips to their associated cylinders, a load being constantly applied to the pipette tips whereby an effective seal is continuously maintained during the entire operation cycle of the apparatus to avoid leaking and contamination of the fluid.

SUMMARY OF THE PRESENT INVENTION

The present invention provides a compact, lightweight apparatus for introducing a measured amount of liquid into receptacles positioned in a microtiter plate through disposable pipettes loaded in a sealed manner on the front end of dispensing air cylinders positioned in the apparatus.

The pipettes, corresponding in number to the number of cylinders, typically 96, are positioned in a carrier tray below the cylinders. The carrier tray is moved in an upward direction by another air cylinder with a sufficient loading force such that the pipettes are sealed to the front end of the adjacent air cylinder. The loading force is maintained during the entire operating sequence of the apparatus ensuring that the pipette tips always have an effective seal with their associated cylinder. O-rings positioned in the carrier tray act as individual springs for each of the individual pipette tips to provide a cushioning effect between the pipette and the adjacent cylinder to compensate for molding variations and other dimensional variations in the pipette tips.

After the pipette tips are secured to the cylinders, they are introduced into the liquid supply and filled with liquid, the liquid thereafter being dispensed into the corresponding receptacle. The pipette tips are removed from the cylinders by the same assembly that loaded the pipette tips and then are disposed of, the pipette loading sequence then being repeated as required by the user.

The apparatus of the present invention uses the air gap dispensing method whereby a vacuum is created with the piston/cylinder to draw fluid into the pipette tips. This prevents contamination from previous fluid dispenses since the fluid does not come in contact with the piston or the cylinder.

The apparatus of the present invention is self-contained in that a separate, additional structure is not necessary to support the loading force. As best illustrated in the aforementioned '426 patent and as will be described in more detail hereinafter, the apparatus is vertically orientated, the loading force also being applied in the vertical direction. Since the apparatus is adapted to move horizontally along a rail mechanism, the pipette tip loading apparatus can be moved horizontally allowing the tips to be loaded at various locations in the horizontal plane.

The present invention thus provides a simple and efficient way of loading pipette tips in a single, integrated assembly while maintaining a continuous loading force on the pipette tips to ensure a tight seal between the pipette tips and the associated loading/dispensing cylinder.

The apparatus is lighter than prior art pipette tip loading devices, and can be easily adapted to robotics and automation because of its portability and the horizontal movement capability of loading the pipette tips and then dispensing the fluid therein.

DESCRIPTION OF THE DRAWING

For a better understanding of the invention as well as other objects and further features thereof, reference is made to the following description which is to be read in conjunction with the accompanying drawings wherein:

FIG. 1 is a front plan view of the apparatus of the present invention;

FIG. 2 is a side plan of the apparatus shown in FIG. 1;

FIG. 3 is a bottom plan view of the apparatus shown in FIG. 1;

DESCRIPTION OF THE INVENTION

Figure 5:
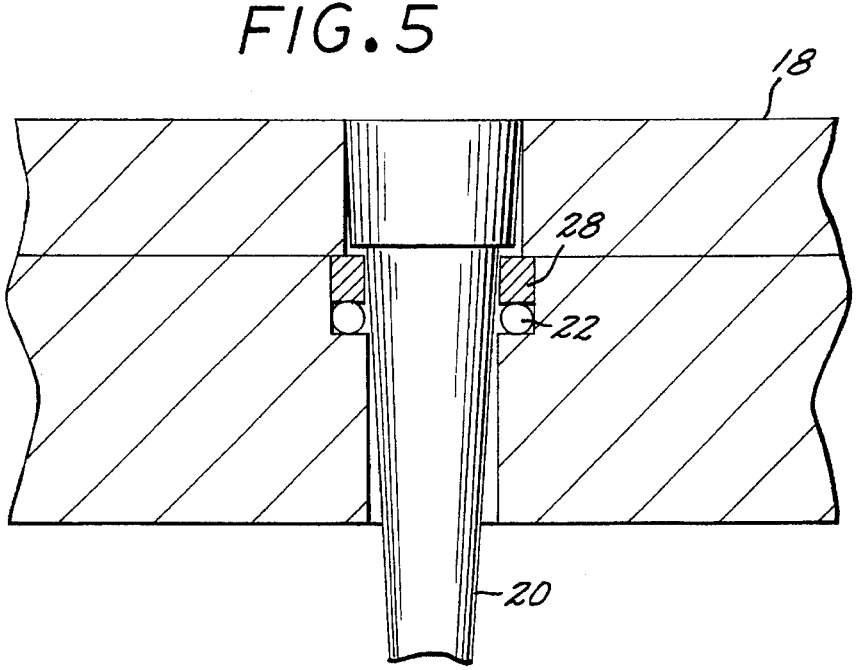
FIG. 5 is a partial sectional view of the pipette tip and pipette tip plate holder.

Referring now to FIGS. 1 and 2, front and side plan views of the apparatus 10 of the present invention are illustrated. Apparatus 10 comprises a plurality of plate members either fixed on support shafts 12 and 14 (four shafts each are provided in the apparatus) or movable in the vertical direction along the support shafts (it should be noted that the black dot symbolizes that the component is fixed to its associated shaft). A pipette tip plate holder 16, movable along shafts 12, is typically arranged to support pipette plate 18. Pipette tip plate 18 is arranged to carry 96 disposable pipette tips 20 and has built-in O-rings 22 with a precision washer 28 associated with each tip (FIG. 5). The O-rings 22 act as individual springs, transmitting the loading force from the plate 18 into the pipette tips 20 carried by plate 16 and into the associate cylinder 26 supported in cylinder plate 24 (actually, twelve cylinders (and associated pistons) would be seen in the FIG. 1 view, and eight cylinders (and associated pistons) would be seen in the FIG. 2 view). The O-rings 22 compensate for the molding variations in the pipette tips 20 and other variations in pipette tip dimensions.

Figure 6:
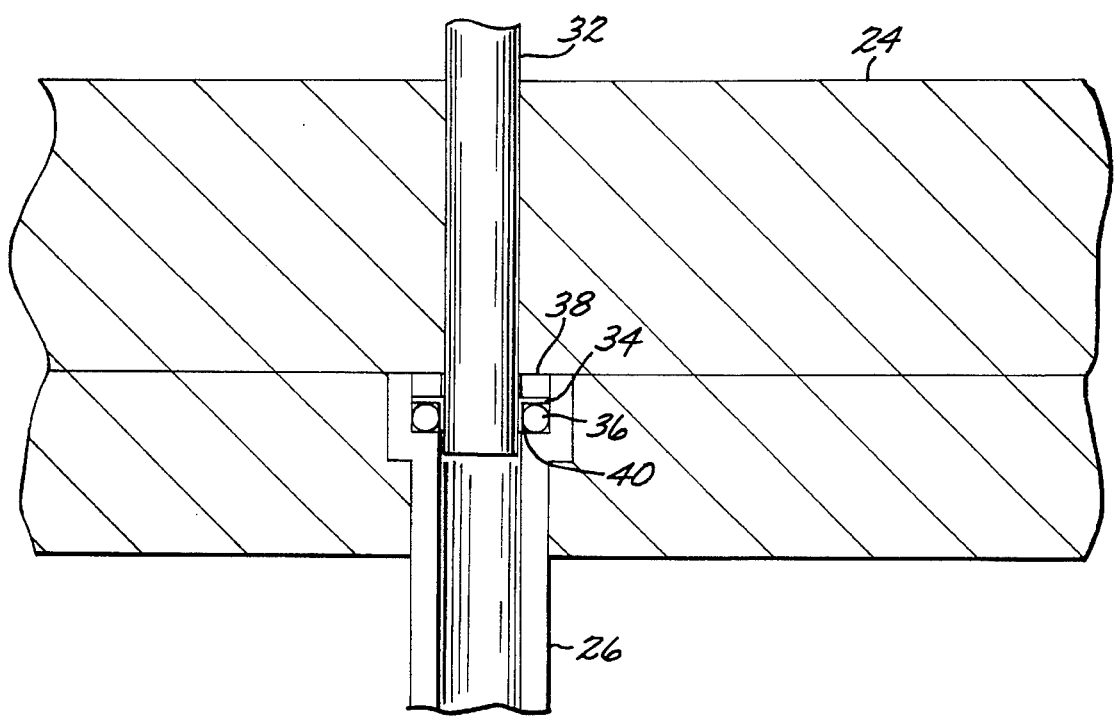
FIG. 6 is a partial sectional view of the cylinder plate portion of the apparatus of FIG. 1.

Cylinders 26 in cylinder plate 24 are attached to cylinder mounting plate 30 which is fixed to shafts 14. Pistons 32 are movable in the vertical direction (up/down) within the fixed cylinders 26. Each piston 32 passes through a teflon seal 34, seal 34 having radial pressure applied to it by compressed O-rings 36 thus maintaining a constant pressure between the seals 34 and the associated piston 32 (FIG. 6). Precision washers 38 are positioned on top of seals 34 to provide downward (axial) pressure against seals 34, O-rings 36 and into the machined recess 40 within cylinders 26. The seal assembly thus formed provides a high quality, long-life seal.

The pistons 32 are connected to piston plate 42 using a ball and socket mechanism 44 (FIG. 4) to provide for accurate alignment. Each piston 32 is allowed to swivel from the centerpoint of the ball joint, thereby automatically adjusting and compensating for slight misalignments between the pistons 32 and associated cylinders 26. The ball end 45 of the pistons are attached to movable piston plate 42. Since the entire piston and cylinder assembly can be removed from apparatus 10, removable piston plate 42 is fixed to a large plate 46 that slides up and down along shafts 14.

Figure 4:
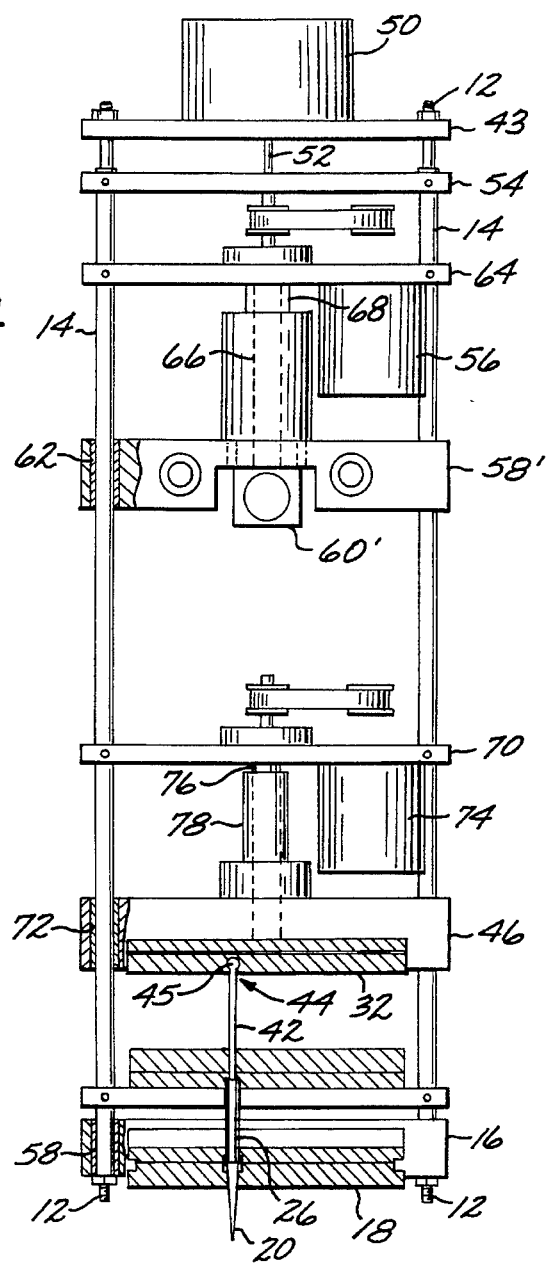
FIG. 4 is a more detailed sectional view of FIG. 1.

Shafts 12 are attached to loader plate 48 at the top of apparatus 10 as illustrated. The base of an actuator 50 is mounted on top of loader plate 48 while the actuator arm 52 is attached to a fixed plate 54. The extension of arm 54 causes plate 48 and shafts 12 to rise in relation to plate 54, which in turn causes plate holder 16 and pipette tip plate 18 to rise in relation to fixed plate 24 along shaft 14 (linear bearings 58 surround shaft 14 as illustrated in FIG. 4) thus loading the tips 20 onto the cylinders 26.

Figure 7:
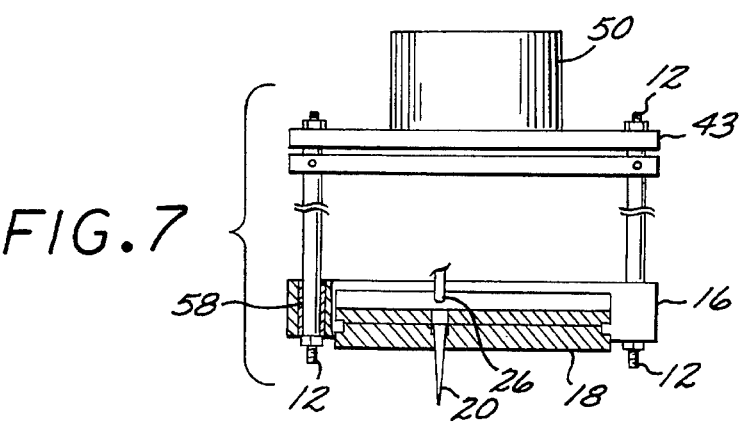
FIG. 7 is similar to FIG. 4 illustrating how the pipette tips are removed from the dispensing cylinders.

Plate holder 16 has dual functions—the loading operation as described hereinabove and as a removal, or stripper plate. In this second function, when plate holder 16 moves down (as shown in FIG. 7), it pushes pipette tips 20 off their associated cylinders.

FIG. 3 is a bottom view of the apparatus shown in FIG. 1 and illustrates the pipette tip plate 18 and carrier plate 16, the latter fixedly supported to shafts 12 and movable in the vertical direction along shafts 14. The carrier plate 16, as illustrated, is designed to carry 96 pipette tips although plates carrying more or less that number can also be utilized if sized properly to be supported in plate holder 16.

The vertical, or "Z" axis up/down motion is controlled by stepper motor 56. Slide assembly 58 and 60 all have a fixed height in elevation relative to the table top of the apparatus. Mounted on the sides of plate 58 are 4 linear bearings 62 (FIG. 4) with shafts 14 passing therethrough. The "Z" axis stepper motor plate 64 is fixed to shafts 14. Therefore, as stepper motor 56 turns, it turns lead screw 66, the latter being connected to a lead screw nut 68 which in turn is fixed to plate 58. This motion causes stepper motor plate 64 to move up/down in relationship to components 58, 60, etc. Since "Z" axis stepper motor plate 64 is fixed to the shafts 14, this plate can move the entire apparatus in an up/down (vertical) direction.

The fluid dispense motion is similar to the operation described above. Fluid dispense stepper motor plate 70 is fixed to the shafts 14. Piston plate 46 has four linear bearings 72 (FIG. 4) and slides up/down on shafts 14. Therefore, as fluid dispense stepper motor 74 rotates, it in turn rotates fluid dispense lead screw 76 and attached lead screw nut 78 moving piston plate 46/42 up/down (vertically) along the shafts 14. The cylinders 26 are attached to cylinder mounting plate 24 which is fixed to shafts 14. Thus, as the fluid stepper motor 74 rotates, it moves the piston plate 46 up/down. The pistons 32 are moved up/down (vertically) within the fixed cylinders 26.

This motion, in conjunction with the associated seals, causes a vacuum to form in the cylinders 26. This vacuum pulls fluid from a fluid source (not shown) up and into pipette tips 20. This dispensing method uses an "air gap" between the fluid and the pistons 26. Since fluid is not brought into the piston/cylinder configuration because of the air gap and only contacts pipette tips 20, a sterile fluid transfer process is provided.

Roller guides 80 roll on rail plate 82 by way of roller bearings contained within roller guides and rail plate 82 is rigidly attached to supporting member 60 or rail plate 82 to allow the piston dispenser assembly to dispense the fluid at a remote location. Although FIGS. 1 and 2 illustrate a rail type travel arrangement, other configurations can be used, such as the rod and leadscrew structure 58', 60' utilized in FIG. 4.

It should be noted that the pipette tips 20 may or may not be removed after each use but is dependent upon the user's application.

The pipette loading/dispensing cycle is repeated as many times as the user requires.

The pipette tips 20 are under constant load throughout the operating cycle of the apparatus to ensure an effective seal between the pipette tips and cylinders.

FIG. 7 illustrates the situation when plate holder 16 has removed or stripped pipette tips 20 from cylinders 26. In this case, as arm 52 of actuator 50 retracts to the position illustrated, plate 48 is moved towards loader plate 54, causing pipette tip plate holder 16 and pipette tip plate 18 to move lower with respect to cylinder mounting plate 30 to the position illustrated, removing pipettes 20 from their associated cylinders 26.

The present invention thus provides a unique apparatus for loading pipettes to their associated dispensing cylinders and in a manner such that the integrity of the seal therebetween is maintained throughout the liquid dispensing cycle. In addition, the components of the apparatus, such as the cylinders, pipette holding plate and air cylinders, are all contained in one, vertically extending assembly.

While the invention has been described with a reference to its preferred embodiment, it will be understood by those skilled in the art that various changes may be made and equivalents may be substituted for elements thereof without departing from the true spirit and scope of the invention. In addition, modifications may be made to adapt a particular situation or material to the teachings of the invention without departing from its essential teachings.

What is claimed is:

1. Apparatus for dispensing predetermined amounts of liquid into receptacles comprising:

first and second sets of vertically extending shafts;

a plate member supported by said first set of shafts and positioned at the uppermost extent thereof;

actuator means positioned on said plate member;

a pipette tip plate for supporting a plurality of pipette tips;

a plate holder for holding said pipette plate, said plate holder being movable along said second set of shafts;

a cylinder mounting plate having a plurality of dispensing cylinders attached thereto, said cylinder mounting plate being fixedly attached to said second set of shafts; and means to energize said actuator means whereby said plate holder is moved upwardly in a manner such that the pipette tips are positioned into sealing engagement with an associated cylinder.

2. The apparatus of claim 1 wherein said pipette tip plate comprises a plurality of O-rings supported in an internal recess, the pipette tips in turn being supported by its associated O-ring.

3. The apparatus of claim 1 wherein said actuator means is energized in a manner whereby said plate holder moves in the downward direction causing said pipette tips to be pushed off the associated cylinders.

4. The apparatus of claim 1 further including a piston plate movable along said second set of shafts having a plurality of piston members supported therein, said piston members being positioned for upward or downward movement within an associated cylinder.

5. The apparatus of claim 4 further including actuator means for moving said piston plate in an upwards direction whereby said liquid is drawn into said pipette tips.

6. The apparatus of claim 5 wherein said actuator means moves said piston plate in a downwards direction whereby said liquid is dispensed into said receptacles.

7. The apparatus of claim 6 wherein the liquid in said pipette tips is separated from said cylinder by an air gap.

* * * * *